(12) United States Patent
Choi et al.

(10) Patent No.: US 10,337,016 B2
(45) Date of Patent: Jul. 2, 2019

(54) PHARMACEUTICAL COMPOSITION FOR TREATMENT OF CANCER COMPRISING RNA OLIGONUCLEOTIDE

(71) Applicant: KOREA ADVANCED INSTITUTE OF SCIENCE AND TECHNOLOGY, Daejeon (KR)

(72) Inventors: Byong-Seok Choi, Daejeon (KR); Suk-Jo Kang, Daejeon (KR); Janghyun Lee, Daejeon (KR); Ji Youn Min, Daejeon (KR); Dongmin Chun, Daejeon (KR); Si-Eun Sung, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/327,596

(22) PCT Filed: Oct. 14, 2016

(86) PCT No.: PCT/KR2016/011571
§ 371 (c)(1),
(2) Date: Jan. 19, 2017

(87) PCT Pub. No.: WO2017/065563
PCT Pub. Date: Apr. 20, 2017

(65) Prior Publication Data
US 2017/0306330 A1    Oct. 26, 2017

(30) Foreign Application Priority Data

Oct. 15, 2015 (KR) .......... 10-2015-0144306
Jul. 6, 2016 (KR) .......... 10-2016-0085582

(51) Int. Cl.
*C12N 15/117* (2010.01)
*A61K 31/713* (2006.01)
*C12N 15/113* (2010.01)

(52) U.S. Cl.
CPC .......... *C12N 15/117* (2013.01); *A61K 31/713* (2013.01); *C12N 15/113* (2013.01); *C12N 15/1131* (2013.01); *C12N 2310/17* (2013.01); *C12N 2310/31* (2013.01); *C12N 2310/315* (2013.01); *C12N 2310/531* (2013.01); *Y02A 50/385* (2018.01); *Y02A 50/393* (2018.01)

(58) Field of Classification Search
None
See application file for complete search history.

(56) References Cited

U.S. PATENT DOCUMENTS 7,691,997 B2 * 4/2010 Khvorova ............ A61K 31/713
                                                      536/24.5
2012/0121551 A1   5/2012 Hartmann et al. ........... 424/93.7
(Continued)

OTHER PUBLICATIONS

Schwappacher et al., cGMP-dependent protein kinase Iβ regulates breast cancer cell migration and invasion via interaction with the actin/myosin-associated protein caldesmon. J Cell Sci. Apr. 1, 2013; 126(7): 1626-1636. (Year: 2013).*

(Continued)

*Primary Examiner* — Kevin K Hill
*Assistant Examiner* — Arthur S Leonard
(74) *Attorney, Agent, or Firm* — Harness, Dickey & Pierce, P.L.C.

(57) ABSTRACT

The present disclosure provides a pharmaceutical composition for treating cancer comprising an RNA oligonucleotide having a particular sequence and structure. Specifically, when a cell line is treated with an RNA oligonucleotide having specific sequence and helical bend structure according to the present disclosure, the expression of ISG56 is (Continued)

increased and apoptosis of cancer cells is induced. Thus, a composition comprising the RNA oligonucleotide can be used as an anticancer agent.

19 Claims, 9 Drawing Sheets

Specification includes a Sequence Listing.

(56) References Cited

U.S. PATENT DOCUMENTS

| | | | |
|---|---|---|---|
| 2012/0288476 A1 | 11/2012 | Hartmann et al. | 424/85.4 |
| 2016/0017334 A1* | 1/2016 | Hiscott | A61K 39/12 |
| | | | 424/209.1 |
| 2018/0169222 A1* | 6/2018 | Lopez | A61P 31/14 |

OTHER PUBLICATIONS

University of Rochester Medical Center, RNA structure web base software, pp. 1-5, on-line Aug. 4, 2012, https://rna.urmc.rochester.edu/RNAstructureWeb/Servers/Predict1/Predict1.html (Year: 2012).*

Dharmacon Product Sheet, 2'-ACE RNA Synthesis Chemistry, pp. 1-3, on-line Feb. 1, 2001, http://dharmacon.horizondiscovery.com/uploadedFiles/Resources/2-ace-rna-synth-chem-technote.pdf. (Year: 2001).*

Ahmed F, Raghava GPS (2011) Designing of Highly Effective Complementary and Mismatch siRNAs for Silencing a Gene. PLoS ONE 6(8): e23443. pp. 1-8 (Year: 2011).*

Yoshida et al., (2004). "Interferonβ gene therapy for cancer: basic research to clinical application" *Cancer Sci.*, 95(11):858-865.

\* cited by examiner

SEQUENCE LISTING

```
<160> NUMBER OF SEQ ID NOS: 12

<210> SEQ ID NO 1
<211> LENGTH: 8
<212> TYPE: RNA
<213> ORGANISM: Artificial Sequence
<220> FEATURE:
<223> OTHER INFORMATION: RNA oligonucleotide
<220> FEATURE:
<221> NAME/KEY: misc_feature
<222> LOCATION: (1)..(1)
<223> OTHER INFORMATION: A, G, C or U
<220> FEATURE:
<221> NAME/KEY: misc_feature
<222> LOCATION: (7)..(8)
<223> OTHER INFORMATION: A, G, C or U

<400> SEQUENCE: 1 nguagann                                                            8
```

```
<210> SEQ ID NO 2
<211> LENGTH: 8
<212> TYPE: RNA
<213> ORGANISM: Artificial Sequence
<220> FEATURE:
<223> OTHER INFORMATION: RNA oligonucleotide
<220> FEATURE:
<221> NAME/KEY: misc_feature
<222> LOCATION: (1)..(2)
<223> OTHER INFORMATION: A, G, C or U
<220> FEATURE:
<221> NAME/KEY: misc_feature
<222> LOCATION: (8)..(8)
<223> OTHER INFORMATION: A, G, C or U

<400> SEQUENCE: 2 nnuuugcn                                                                    8

<210> SEQ ID NO 3
<211> LENGTH: 8
<212> TYPE: RNA
<213> ORGANISM: Artificial Sequence
<220> FEATURE:
<223> OTHER INFORMATION: RNA oligonucleotide

<400> SEQUENCE: 3 gguagacg                                                                    8

<210> SEQ ID NO 4
<211> LENGTH: 8
<212> TYPE: RNA
<213> ORGANISM: Artificial Sequence
<220> FEATURE:
<223> OTHER INFORMATION: RNA oligonucleotide

<400> SEQUENCE: 4 cguuugcc                                                                    8

<210> SEQ ID NO 5
<211> LENGTH: 33
<212> TYPE: RNA
<213> ORGANISM: Artificial Sequence
<220> FEATURE:
<223> OTHER INFORMATION: iav RNA oligonucleotide

<400> SEQUENCE: 5
gaguagaaac aaggcuucgg ccugcuuuug cuc                                       33

<210> SEQ ID NO 6
<211> LENGTH: 20
<212> TYPE: RNA
<213> ORGANISM: Artificial Sequence
<220> FEATURE:
<223> OTHER INFORMATION: Cont-GC-8bp RNA oligonucleotide

<400> SEQUENCE: 6
ggcagacguu cgcgucugcc                                                      20

<210> SEQ ID NO 7
<211> LENGTH: 20
<212> TYPE: RNA
<213> ORGANISM: Artificial Sequence
<220> FEATURE:
<223> OTHER INFORMATION: Bend-GC-8bp-PS RNA oligonucleotide

<400> SEQUENCE: 7
gguagacguu cgcguuugcc                                                      20
```

```
<210> SEQ ID NO 8
<211> LENGTH: 89
<212> TYPE: RNA
<213> ORGANISM: Artificial Sequence
<220> FEATURE:
<223> OTHER INFORMATION: Long_Bend RNA oligonucleotide

<400> SEQUENCE: 8
gguagacgaa accagauaaa aaaaaaaaaa aaaaaaaaaa aaauaauuuu uuuuuuuuuu      60
uuuuuuuuuu uuaucugguu ucguuugcc                                        89

<210> SEQ ID NO 9
<211> LENGTH: 22
<212> TYPE: DNA
<213> ORGANISM: Artificial Sequence
<220> FEATURE:
<223> OTHER INFORMATION: ISG56 forward primer

<400> SEQUENCE: 9
gcctccttgg gttcgtctac aa                                               22

<210> SEQ ID NO 10
<211> LENGTH: 22
<212> TYPE: DNA
<213> ORGANISM: Artificial Sequence
<220> FEATURE:
<223> OTHER INFORMATION: ISG56 reverse primer

<400> SEQUENCE: 10
tcaaagtcag cagccagtct ca                                               22

<210> SEQ ID NO 11
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 11
gcattgccct caacgaccac                                                  20

<210> SEQ ID NO 12
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 12
gaggccatgt gggccatgag                                                  20
```

PHARMACEUTICAL COMPOSITION FOR TREATMENT OF CANCER COMPRISING RNA OLIGONUCLEOTIDE

CROSS-REFERENCE TO RELATED APPLICATIONS

This application is a national phase application of PCT Application No. PCT/KR2016/011571, filed on Oct. 14, 2016, which claims the benefit and priority of Korean Patent Application No. 10-2016-0085582, filed Jul. 6, 2016, which claims priority to Korean Patent Application No. 10-2015-0144306, filed Oct. 15, 2015. The entire disclosures of the applications identified in this paragraph are incorporated herein by reference.

FIELD

The present disclosure relates to a pharmaceutical composition for treating cancer comprising an RNA oligonucleotide having a particular sequence and structure.

BACKGROUND ART

Cells divide and grow by their own regulation system, and they maintain balance of the overall number in a body by apoptosis, which occurs when cells reach their lifespan or get damaged. However, uncontrolled proliferation of cells due to failure of cells' own regulation system may cause an invasion of the cells into adjacent normal tissues and organs to form a tumor, thereby destroying or distorting the normal tissues and organs. This state is called cancer. Cancer therapies include surgery, radiotherapy, chemotherapy, and so on, but, several problems such as low cure rates and many side effects, etc. have been reported. Thus, a development of new anticancer drug that can reduce the side effects and increase the cure rates is required.

It is known that the incidence of pancreatic cancer is low compared with other cancers, but it has the highest mortality among cancer patients. The mortality of the pancreatic cancer is increasing because of difficulty in early diagnosis and easy metastasis to the surrounding organs or lymph nodes.

Chemotherapy and radiotherapy are used to treat the pancreatic cancer. Gemcitabine, which is most widely used anti-pancreatic cancer drug, is used with other drugs such as oxalate, 5-FU (5-fluorouracil), and so on. However, it does not have much effect on significant increase of the survival rate of pancreatic cancer patients.

Recently, research is being carried out to treat various disorders by using an RNA oligonucleotide. U.S. Patent Application Publication No. 2012/0288476 discloses that an uncapped oligonucleotide having a phosphate group at the 5'-end can increase the expression of type 1 interferon, interleukin-18, and interleukin-1β, etc.

In addition, U.S. Patent Application Publication No. 2012/0121551 discloses that an RNA consisting of four nucleotides can promote immune responses by inducing the activation of interferon-α.

The RNAs mentioned above have a common feature that they all have a triphosphate group at the 5'-end. It has been known in the art that an uncapped RNA which has a triphosphate group at the 5'-end can activate the expression of interferon by binding to intracellular retinoic acid-inducible gene-I (RIG-I) protein.

Interferon is a glycoprotein derived from most of the cells having a nucleus. Interferon was known as an important factor in suppressing tumor growth since it was reported that interferon-α and interferon-β genes of type 1 interferon gene cluster were deleted in tumor cells. Recombinant interferon-β has been used as an anticancer drug from the 1980s (Jun Yoshida et al., *Cancer Sci.*, 2004, Vol. 95, No. 11, 858-865).

DISCLOSURE

Technical Problem

The present inventors have endeavored diligently to find a substance applicable to treat cancer, and surprisingly and unexpectedly discovered that an RNA oligonucleotide which does not have a triphosphate group at the 5'-end can also increase the expression of interferon stimulated gene 56 (ISG56) expressed by interferon-β if the RNA oligonucleotide has a specific sequence and structure, and induce apoptosis of cancer cells.

Accordingly, an object of the present disclosure is to provide a pharmaceutical composition for treating cancer comprising an RNA oligonucleotide having a particular sequence and structure.

Technical Solution

The present disclosure provides a pharmaceutical composition for treating cancer comprising an RNA oligonucleotide as an active ingredient, wherein the RNA oligonucleotide comprises the base sequence represented by SEQ ID NO:1 (5'-$N_1$GUAGA$N_2N_3$-3') and the base sequence represented by SEQ ID NO:2 (5'-$N_4N_5$UUUGC$N_6$-3') wherein the base sequences are bound to each other by a complementary binding to form double strands having a helical bend structure; the 3'-end of the base sequence represented by SEQ ID NO:1 and the 5'-end of the base sequence represented by SEQ ID NO:2 are connected into a loop to form a hairpin structure; and the base sequence represented by SEQ ID NO:1 has a hydroxy (OH) group at the 5'-end thereof.

Advantageous Effects

When a cell line is treated with an RNA oligonucleotide having a particular sequence and helical bend structure according to the present disclosure, the expression of ISG56 is increased and apoptosis of cancer cells is induced. Thus, a composition comprising such RNA oligonucleotide can be used as an anticancer agent.

BEST MODE

Figure 1:
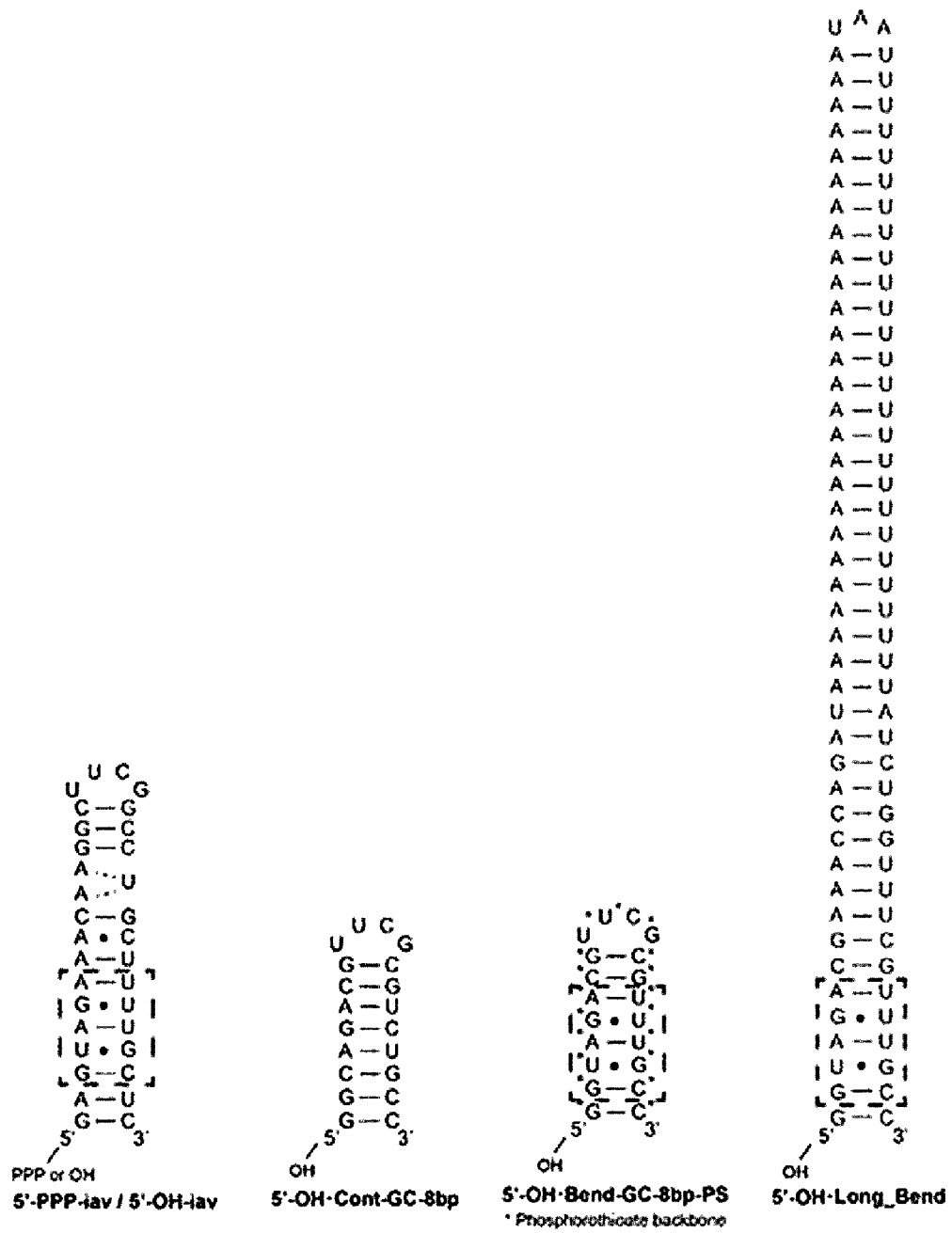
FIG. 1 shows the sequences and structures of RNA oligonucleotides prepared according to an example of the present disclosure.

Hereinafter, the present disclosure will be described in detail.

The present disclosure provides a pharmaceutical composition for treating cancer comprising an RNA oligonucleotide as an active ingredient, wherein the RNA oligonucleotide comprises the base sequence represented by SEQ ID NO:1 (5'-$N_1$GUAGA$N_2N_3$-3') and the base sequence represented by SEQ ID NO:2 (5'-$N_4N_5$UUUGC$N_6$-3') wherein the base sequences are bound to each other by a complementary binding to form double strands having a helical bend structure; the 3'-end of the base sequence represented by SEQ ID NO:1 and the 5'-end of the base sequence represented by SEQ ID NO:2 are connected into a loop to form a hairpin structure; and the base sequence represented by SEQ ID NO:1 has a hydroxy (OH) group at the 5'-end thereof.

An RNA oligonucleotide according to the present disclosure may have 8 to 100, 8 to 50, 8 to 30, 8 to 20, 10 to 100, 10 to 50, 10 to 30, 20 to 500, 20 to 300, 10 to 200, 10 to 100, 20 to 100, 20 to 90, or 20 to 50 bases.

In the base sequence represented by SEQ ID NO:1 or SEQ ID NO:2 which forms the RNA oligonucleotide, $N_1$ to $N_6$ may be one selected from the group consisting of A, G, C and U. Specifically, $N_1$ to $N_6$ may be G or C. In one example of the present disclosure, $N_1$ may be G, $N_2$ may be C, and $N_3$ may be G in the base sequence represented by SEQ ID NO:1 (corresponding to SEQ ID NO:3); and $N_4$ may be C, $N_5$ may be G, and $N_6$ may be C in the base sequence represented by SEQ ID NO:2 (corresponding to SEQ ID NO:4).

An RNA oligonucleotide of the present disclosure may form a helical bend structure between the fourth base (A) of the base sequence represented by SEQ ID NO:1 and the fifth base (U) of the base sequence represented by SEQ ID NO:2.

In one example of the present disclosure, the helical bend structure is formed between the fourth base (A) of the base sequence represented by SEQ ID NO:1 and the fifth base (U) of the base sequence represented by SEQ ID NO:2 when the third base (U) and the fifth base (G) of the base sequence represented by SEQ ID NO:1 and the sixth base (G) and the fourth base (U) of the base sequence represented by SEQ ID NO:2 respectively form wobble base pairs.

The helical bend structure may have a shape bent in 10 to 90 degrees relative to the plane formed by the double-stranded RNA, particularly 30 to 70 degrees, and more particularly 40 to 50 degrees.

In the hairpin structure, the loop may be composed of at least 4 bases, for instance, 4 to 80, 4 to 75, 4 to 70, 4 to 65, 4 to 60, 4 to 55, 4 to 50, 4 to 45, 4 to 40, 4 to 35, 4 to 30, 4 to 25, 4 to 20, 4 to 15, or 4 to 10 bases. In one example of the present disclosure, the loop may be composed of 4 or 73 bases. In one example of the present disclosure, the four bases constituting the loop may be UUCG.

Also, if some of the base sequences constituting the loop are complementary to each other, they may form a stem structure by Watson-Crick base pairing. The stem structure may include AU motif in which A and U forms a Watson-Crick base pair.

Herein, the AU motif may be composed of 10 to 50, 15 to 40, 20 to 35, or 25 to 30 AU base pairs. In an example of the present disclosure, the AU motif may be composed of 26 consecutive AU base pairs.

In one example of the present disclosure, the RNA oligonucleotide having the hairpin structure may be the base sequence represented by SEQ ID NO:7 or SEQ ID NO:8.

In the RNA oligonucleotide according to the present disclosure, at least one of the phosphodiester bonds in the RNA oligonucleotide may be changed to at least one selected from the group consisting of a phosphorothioate bond, a boranophosphate bond and a methylphosphonate bond, in order to inhibit degradation by endonuclease and improve in vivo stability. In a specific example of the present disclosure, at least one of the phosphodiester bonds may be changed to the phosphorothioate bond.

Figure 3:
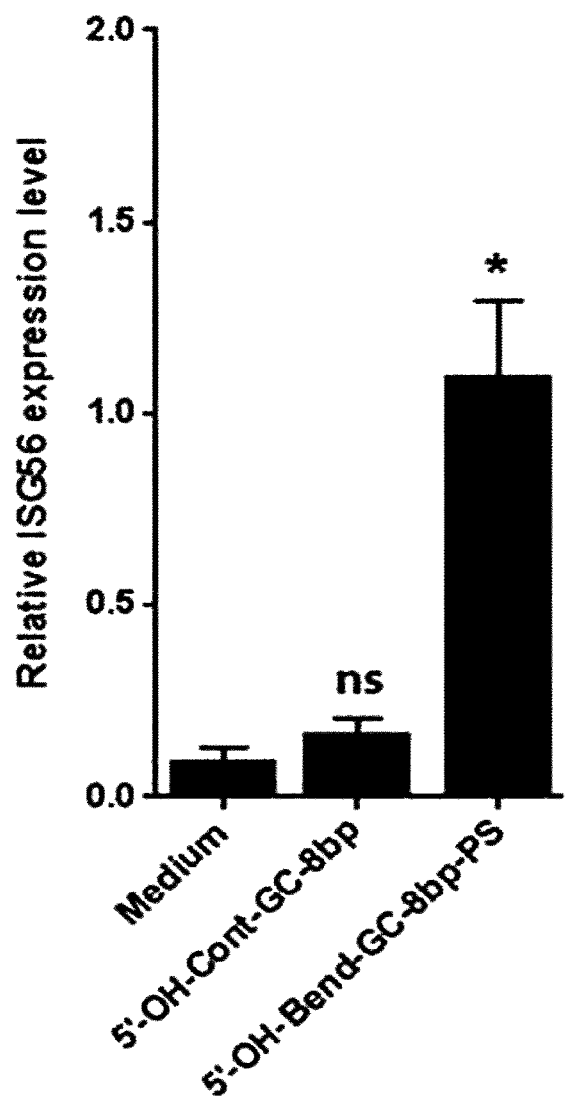
FIG. 3 is a graph showing the increase of ISG56 expression level by 5'-OH-Bend-GC-8 bp-PS, an RNA oligonucleotide prepared according to an example of the present disclosure.
Figure 4:
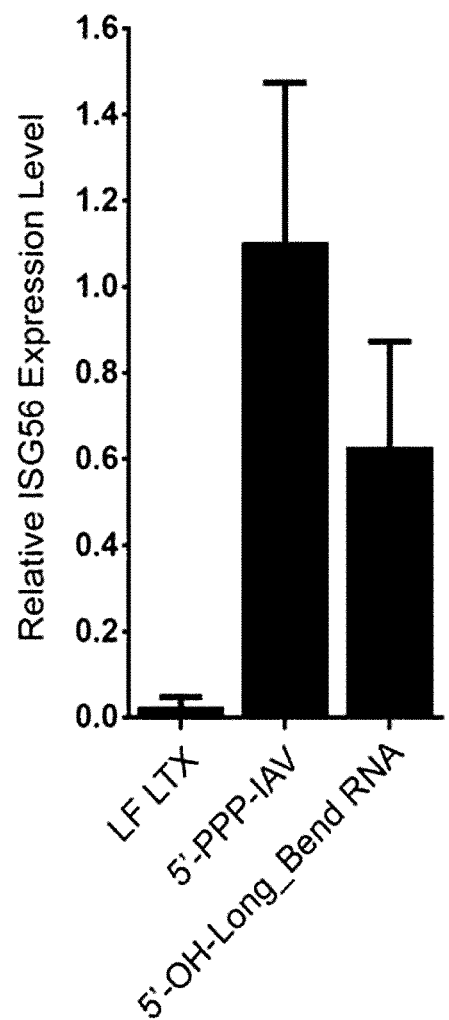
FIG. 4 is a graph showing the increase of ISG56 expression level by 5'-OH-Long_Bend, an RNA oligonucleotide prepared according to an example of the present disclosure.

The present inventors have prepared RNA oligonucleotides having hairpin RNA structure (FIG. 1). Among them, 5'-OH-iav or 5'-PPP-iav were found to have a helical bend structure (FIG. 2) and to increase the expression of ISG56 (FIGS. 3 and 4).

Also, an RNA oligonucleotide having the helical bend structure was found to induce apoptosis of pancreatic cancer, liver cancer, and stomach cancer cell lines without inducing apoptosis of normal cells (FIGS. 5 to 8B).

Accordingly, since an RNA oligonucleotide having a helical bend structure of the present disclosure increases the expression of ISG56 and induces apoptosis of cancer cells, a composition comprising the RNA oligonucleotide can be used for cancer treatment.

The pharmaceutical composition for treating cancer of the present disclosure can be used to treat various cancers such as pancreatic cancer, liver cancer, stomach cancer, lung cancer, colorectal cancer, rectal cancer, thyroid cancer, esophageal cancer, renal caner, bladder cancer, prostate cancer, cervical cancer, breast cancer, hematologic malignancy, skin cancer, epithelial cancer, brain cancer, central nerves cancer, or ovarian cancer, etc.

The aforementioned pharmaceutical composition for treating cancer may comprise an RNA oligonucleotide of the present disclosure as an active ingredient in an amount of 10 to 95 weight % based on the total weight of the pharmaceutical composition. In addition, the pharmaceutical composition of the present disclosure may comprise one or more other active ingredients with the same or similar function in addition to the aforementioned active ingredient.

The pharmaceutical composition of the present disclosure may comprise one or more pharmaceutically acceptable additives, for example, excipients, carriers, diluents, and other adjuvants, etc. for the administration.

The dosage of the pharmaceutical composition of the present disclosure may be adjusted based on various factors such as type and severity of a disease, type and amount of an active ingredient and other ingredients comprised in the composition, type of a formulation, and age, weight, general health condition, sex and diet of the patient, time of administration, route of administration, treatment period, and drugs simultaneously used, etc. However, to achieve a desired effect, the effective amount of an RNA oligonucleotide comprised in the pharmaceutical composition of the present disclosure is adjusted to reach the intracellular concentration of 1 to 1,000 nM, specifically 100 to 500 nM. It may be administered in a single dose or divided doses per day.

In addition, the pharmaceutical composition of the present disclosure may be administered to a subject by various methods known in the art. The route of administration can be appropriately selected by taking into consideration the factors such as administration method, volume of body fluid and viscosity, etc.

MODE FOR INVENTION

Hereinafter, the present disclosure is explained in detail by Examples. The following Examples are intended to further illustrate the present disclosure without limiting its scope.

Example 1. Preparation of RNA Oligonucleotides

RNA oligonucleotides which can increase the expression of interferon-β or ISG56 were prepared.

First, RNA oligonucleotides composed of the base sequence represented by SEQ ID NO:5 which have a triphosphate group at the 5'-end were prepared by the techniques known in the art. On the other hand, RNA oligonucleotides composed of one of the base sequences represented by SEQ ID NOS:5 to 8 which have a hydroxy (OH) group at the 5'-end, or RNA oligonucleotides wherein a phosphodiester bond is substituted with a phosphorothioate bond were custom-made at Integrated DNA Technologies or Dharmacon.

As shown in FIG. 1, 5'-OH-iav and 5'-PPP-iav RNA oligonucleotides were prepared, which are composed of the base sequence represented by SEQ ID NO:5. They have a hydroxy group and a triphosphate group at the 5'-ends, respectively. In addition, 5'-OH-Cont-GC-8 bp RNA oligonucleotide was prepared, which is composed of the base sequence represented by SEQ ID NO:6 and has a hydroxy group at the 5'-end. In addition, 5'-OH-Bend-GC-8 bp-PS RNA oligonucleotide was prepared, which is composed of the base sequence represented by SEQ ID NO:7, and has a hydroxy group at the 5'-end, and wherein a phosphodiester bond forming the RNA oligonucleotide is substituted with a phosphorothioate bond. In addition, 5'-OH-Long_Bend RNA oligonucleotide was prepared, which is composed of the base sequence represented by SEQ ID NO:8 and has a hydroxy group at the 5'-end.

Example 2. Verification of Structure of RNA Oligonucleotides

To verify the structures of the 5'-OH-iav and 5'-PPP-iav RNA oligonucleotides prepared in Example 1, the following experiments were carried out.

First, the RNA oligonucleotides prepared in Example 1 were dissolved in a buffer solution containing 10 mM sodium phosphate (pH 6.5), 0.01 mM EDTA, 10 (v/v) % $D_2O$ to prepare a sample, and various spectroscopic experiments were carried out by the methods known in the art. More particularly, two-dimensional NOE spectroscopy (NOESY) was carried out by a nuclear magnetic resonance (NMR) spectroscope (Bruker, USA) of 400, 600 and 800 MHz with the mixing time of 100 and 200 ms. Also, the following experiments were performed: $^1H$-$^{15}H$ heteronuclear single quantum coherence (HSQC) spectroscopic experiment at the temperature of 278 K, double quantum filtered correlated (DQF-COSY) and homonuclear total correlation (TOCSY) spectroscopic experiments with the mixing time of 125 ms, $^1H$-$^{31}P$ heteronuclear correlation (HETCOR) and $^1H$-$^{31}P$ Hetero-TOCSY spectroscopic experiments with the mixing time of 30 ms, and NOESY spectroscopic experiment with the mixing time of 80, 150 and 250 ms. In addition, $^1H$-$^{13}C$ CT-HSQC, HCCH-COSY, 2D HCCH-relayed COSY, 2D HCCH-TOCSY and 3D HCCH-TOCSY spectroscopic experiments were carried out.

As a result of the NMR spectroscopic experiments, the NMR peaks of hydrogens of bases of the RNA oligonucleotides and H1', H2', H3', H4', and H5'/H5" were determined. From the NOESY spectroscopic experiment, approximately 563 NOE distance constraints were obtained, which were divided into 3 to 4 groups according to the distance (e.g., 1.8 to 3.4 Å, 1.8 to 5.0 Å and 3.8 to 7.0 Å; or 1.8 to 3.4 Å, 2.5 Å to 4.5, 3.5 to 6.0 Å and 4.0 to 7.0 Å). As for non-Watson-Crick bonds, no constraints on the hydrogen bonds were used. From the $^3J_{H1', H2'}$ value obtained in DQF-COSY, δ dihedral angle was obtained, and every χ dihedral angle was fixed at −158±15 degrees. Other dihedral angles (for example, α, β, γ, ε, and ζ) were confined to the A-type helical structure of RNA. As for bulge parts, no constraints on the dihedral angles were used except for several β and ε dihedral angles. Residual dipolar coupling values were measured by HSQC experiment whose sensitivity was increased to reach the accuracy of ±1 Hz. In addition, by analyzing the result of the alignment tensor by singular value decomposition, the anisotropy value of −8.0 Hz and the rhombicity value of 0.32 were obtained. Calculation of every structure was carried out by X-PLOR 3.1 and CNS. 100 structures were generated according to the distance constraints, and simulated annealing process was carried out in which the structures were simulated at 3,000 K for 10 ps, and then cooled at 300 K for 50 ps. The distance force constant was kept at 50 kcal/mol/A, and the dihedral angle constant was changed from 20 kcal/mol/A to 400 kcal/mol/A. The structures with the lowest energy state were purified at 300 K for 20 ps, and the last 5 ps were used for a restrained energy minimization. A total of 220 structures obtained from the above procedure were purified by adding 22 residual dipolar coupling values, with the force constant of the residual dipolar coupling value being kept to 3.0 kcal/mol. Ultimately, 32 structures were obtained, which were analyzed by Insight II (Biosym Technologies, USA) and CURVES 5.2 software.

Figure 2:
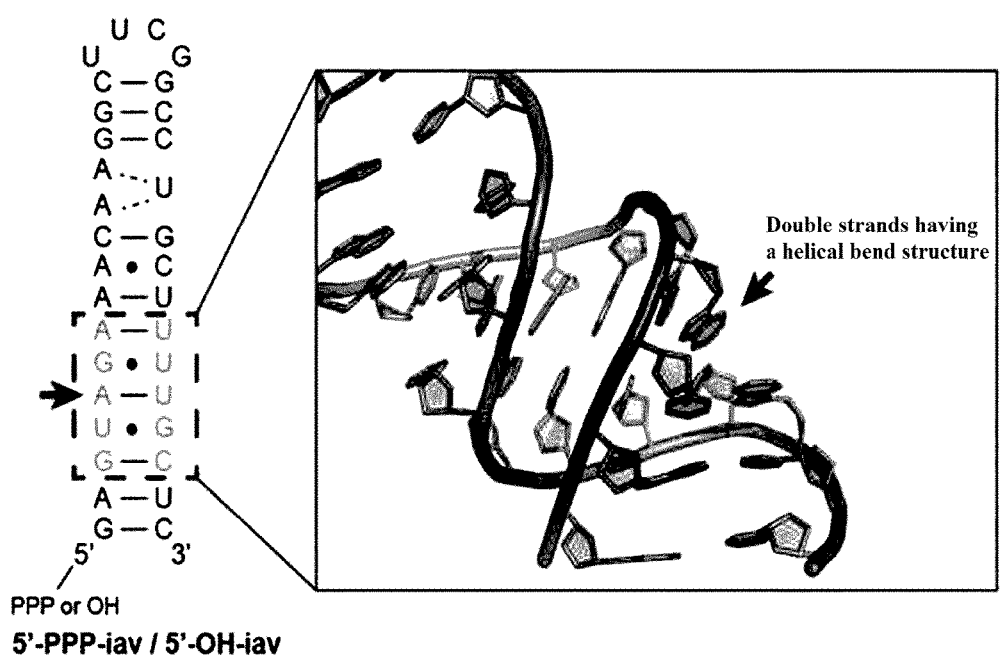
FIG. 2 shows the structure of 5'-OH-iav or 5'-PPP-iav ([SEQ ID NO:5]), an RNA oligonucleotide prepared according to an example of the present disclosure.

As a result, as shown in FIG. 2, it was found that 5'-PPP-iav and 5'-OH-iav RNA oligonucleotides form a helical bend structure. Such a helical bend structure was found to be generated by the formation of double strands through non-Watson-Crick base pairing between two single strands which are respectively composed of the sequences represented by 5'-GUAGA-3' and 5'-UUUGC-3' in the 5'-PPP-iav and 5'-OH-iav RNA oligonucleotides. Thus, it was understood that the RNA oligonucleotides of the present disclosure comprising the sequences represented by 5'-GUAGA-3' and 5'-UUUGC-3', such as 5'-OH-Bend-GC-8 bp-PS and 5'-OH-Long_Bend RNA oligonucleotides also form a helical bend structure.

Experimental Example 1: Verification of Increased ISG56 Expression Level by 5'-OH-Bend-GC-8 bp-PS Expression level of ISG56 induced by the expression of interferon-β was examined to confirm whether the RNA oligonucleotide (5'-OH-Bend-GC-8 bp-PS) containing phosphorothioate bonds among the RNA oligonucleotides having a bend structure prepared in the present disclosure increases the expression of interferon-β.

1.1. Preparation of Cell Line

First, $3\times10^6$ of HEK293T cells (ATCC, USA) were aliquoted into 7 ml of Dulbecco's modified Eagle's medium (DMEM) supplemented with 10% fetal bovine serum (FBS, Gibco, USA) in 100 mm tissue culture plates, and cultured for 24 hours under the condition of 37° C. and 5% $CO_2$ to prepare a cell line.

1.2. Treatment with RNA Oligonucleotides

The cell line prepared in Experimental Example 1.1. was treated with 5'-OH-Bend-GC-8 bp-PS RNA oligonucleotide.

First, the cultured cells were detached by treatment with trypsin-EDTA (Gibco, USA) and the detached cells were counted and aliquoted into 6-well plates at $1\times10^3$ cells/well. Then, the cells were cultured for 42 hours under the condition of 37° C. and 5% $CO_2$. After removing the medium, the cells were treated with 400 μl of OPTI-MEM (Gibco, USA) without FBS, and the RNA oligonucleotide.

RNA oligonucleotide treatment was as follows: each 1 μM of 5'-OH-Cont-GC-8 bp and 5'-OH-Bend-GC-8 bp-PS was mixed with 4 μl of lipofectamine LTX (Invitrogen, USA) and 1.6 μl of plus-reagent (Invitrogen, USA), and 200 μl of resulting mixtures were added to the cells, respectively. Thereafter the cells were incubated for 4 hours under the condition of 37° C. and 5% $CO_2$. The cells for positive control were treated with poly (I:C), known as RIG-I ligand, and those for negative control were treated with culture medium only. After 4 hours, culture medium was removed, and 2 ml of DMEM containing 10% FBS was added to the cells, which were then further incubated for 2 hours under the condition of 37° C. and 5% $CO_2$.

1.3. Verification of ISG56 Expression

To verify the expression of ISG56 in the cells treated with RNA oligonucleotides described above, RNA was isolated according to the following method.

After removing the culture medium, the cells were recovered with 500 μl of TRI-reagent (Ambion, USA), and chloroform was added to the collected cells to separate the RNA layer. Isopropanol was added thereto to make a pellet, and the pellet was washed with 75% ethanol, dried, and dissolved in sterilized distilled water. The separated RNAs were treated with DNase (Promega, USA) for 30 minutes at room temperature to remove contaminated DNAs, and DNase was inactivated by a stop solution. Then, the resultant was treated with Superscript III Reverse Transcriptase (Invitrogen, USA) for 1 hour at 50° C. to synthesize cDNAs from the RNAs.

Using the synthesized cDNA as a template, real-time PCR was carried out. Specifically, real-time PCR was carried out by mixing h-tag DNA polymerase (solgent, Republic of Korea), dNTP, tetraethylammonium chloride, evagreen dye (Biotium, USA), and primers for interferon-β target gene and GAPDH reference gene. Real-time PCR was performed as follows: fixation for 15 minutes at 95° C., then, repeating a set of reactions (20 seconds at 95° C., 40 seconds at 60° C., and 20 seconds at 72° C.) for 40 cycles. The primers for ISG56 and GAPDH are shown in Table 1 below.

TABLE 1

| SEQ ID NO | Name | Sequence |
| --- | --- | --- |
| SEQ ID NO: 9 | ISG56 forward | 5'-gcctccttggg ttcgtctacaa-3' |

TABLE 1-continued

| SEQ ID NO | Name | Sequence |
| --- | --- | --- |
| SEQ ID NO: 10 | ISG56 reverse | 5'-tcaaagtcagc agccagtctca-3' |
| SEQ ID NO: 11 | GAPDH forward | 5'-gcattgccctc aacgaccac-3' |
| SEQ ID NO: 12 | GAPDH reverse | 5'-gaggccatgtg ggccatgag-3' |

The changes in the ISG56 expression level are shown in the graph of FIG. 3.

As shown in FIG. 3, it was found that 5'-OH-Bend-GC-8 bp-PS RNA oligonucleotide having a helical bend structure with a hydroxy group at the 5'-end increased the ISG56 expression to a significant level.

Experimental Example 2: Verification of ISG56 Expression by 5'-OH-Long_Bend

Among the RNA oligonucleotides having a bend structure prepared in the present disclosure, it was examined whether the RNA oligonucleotide (5'-OH-Long_Bend) having a long-length hairpin structure can increase the interferon-6 expression by assessing changes in the ISG56 expression.

All experiments were performed by the same method as Experimental Example 1. The cells for negative control were treated with the culture medium only, while those for positive control were treated with 5'-PPP-iav. The cells of experimental groups were treated with 5'-OH-Long_Bend RNA oligonucleotide.

The changes in the ISG56 expression are shown in the graph of FIG. 4.

As shown in FIG. 4, it was found that 5'-OH-Long_Bend RNA oligonucleotide, which has a hydroxy group at the 5'-end, a helical bend structure and a long-length hairpin, increased the ISG56 expression to a significant level.

Experimental Example 3: Verification for Apoptosis Inducement Effect of Pancreatic Cancer Cells by 5'-OH-Bend-GC-8 bp-PS and 5'-OH-Long_Bend RNA Oligonucleotides 3.1. Preparation of Cell Line and Treatment with RNA Oligonucleotides First, $0.5\times10^5$ of Panc02 cells (Prof. Dr. med. Christiane Bruns, Universittsklinikum Magdeburg), 2×vitamin (Gibco, USA) that was 50-fold diluted, and 300 μl of DMEM (Dulbecco's modified Eagle's medium; WELGENE, USA) containing 2×NEAA (Non-essential Amino Acid solution; Sigma, USA) were aliquoted into each well of 24-well plates.

1 μg/mL of RNA oligonucleotide (5'-OH-Bend-GC-8 bp-PS or 5'-OH-Long_Bend) and poly(I:C) (Invivogen, USA) were mixed with 40 μl of OPTI-MEM (Gibco, USA), respectively. 1 μl of lipofectamine LTX (Invitrogen, USA) and 0.6 μl of plus-reagent (Invitrogen, USA) were mixed and 40 μl of OPTI-MEM (Gibco, USA) was added to the mixture, and then the mixture was incubated for 5 minutes at room temperature. After that, each 40 μl of RNA oligonucleotides prepared and poly(I:C) mixture was mixed with 40 μl mixture of lipofectamine and plus reagent, respectively. The mixture was incubated for 20 minutes at room temperature to combine RNA oligonucleotides or Poly I:C with lipofectamine.

Then, 80 μl of the combined RNA oligonucleotide and lipofectamine was injected into wells containing Panc02 cells and the cells were cultured for 24 hours under the condition of 37° C. and 5% $CO_2$. The cells for positive control were treated with poly(I:C), known as RIG-I ligand, and those for negative control were treated with culture medium and 5'-OH-Cont-GC-8 bp only.

3.2. Verification of Apoptosis Using FACS (Fluorecence-Activated Cell Sorting)

As Experimental Example 3.1, a cell line treated with an RNA oligonucleotide or poly(I:C) was collected into a 5 mL round-bottom tube using 0.25% trypsin-EDTA (Gibco, USA), and then the supernatant was removed by spinning down for 5 minutes at 4° C. under the speed of 1500 rpm. Then, the cells were dyed with 100 μl of 1×combined buffer (10 mM HEPES, 140 mM NaCl, 2.5 mM $CaCl_2$) containing Annexin V combined with FITC (Biolegend, USA) and 7-aminoactinomycin D (7-AAD; BD Bioscience, USA) for 15 minutes in the darkroom. After that, the dyed cells were measured with LSRFortessa flow cytometry (BD Bioscience, USA) and the result was analyzed using FlowJo software (Treestar, USA).

Figure 5:
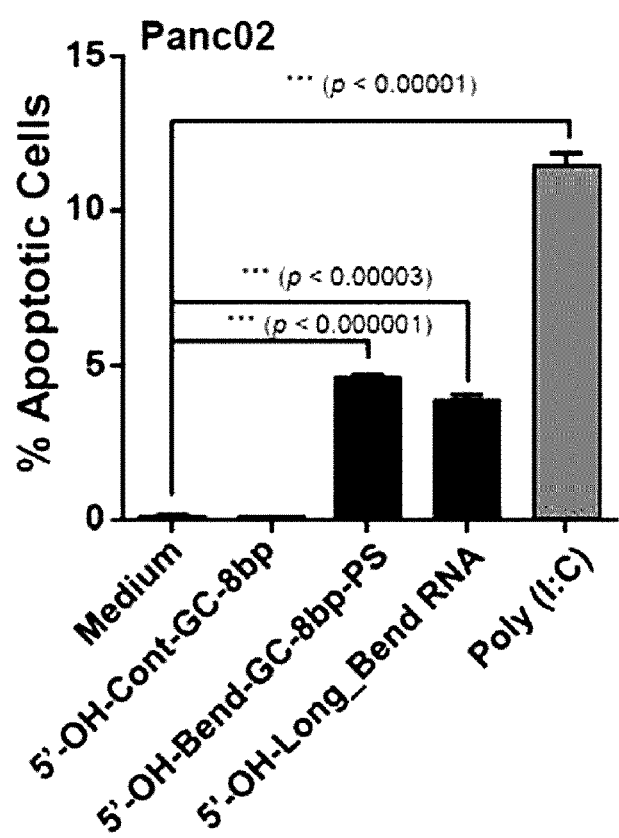
FIG. 5 is a graph showing the apoptosis inducement effect of pancreatic cancer cell line (Panc02) using FACS by 5'-OH-Bend-GC-8 bp-PS and 5'-OH-Long_Bend, RNA oligonucleotides prepared according to an example of the present disclosure.

The rate of apoptotic cells is shown in the graph of FIG. 5.

As shown in FIG. 5, it was found that 5'-OH-Bend-GC-8 bp-PS RNA oligonucleotide and 5'-OH-Long_Bend RNA oligonucleotide having a bend structure with a hydroxy group at the 5'-end induced apoptosis of pancreatic cancer cell line to a significant level.

Experimental Example 4: Verification for Apoptosis Inducement Effect of Normal Cells by 5'-OH-Bend-GC-8 bp-PS and 5'-OH-Long_Bend RNA Oligonucleotides In accordance with the procedure of Experimental Example 3.1, normal cell line (HEK293; ATCC, USA) was aliquoted in DMEM (WELGENE, USA) and RNA oligonucleotides were treated thereto. Then, the apoptosis inducement effect was investigated using FACS as Experimental Example 3.2.

Figure 6:
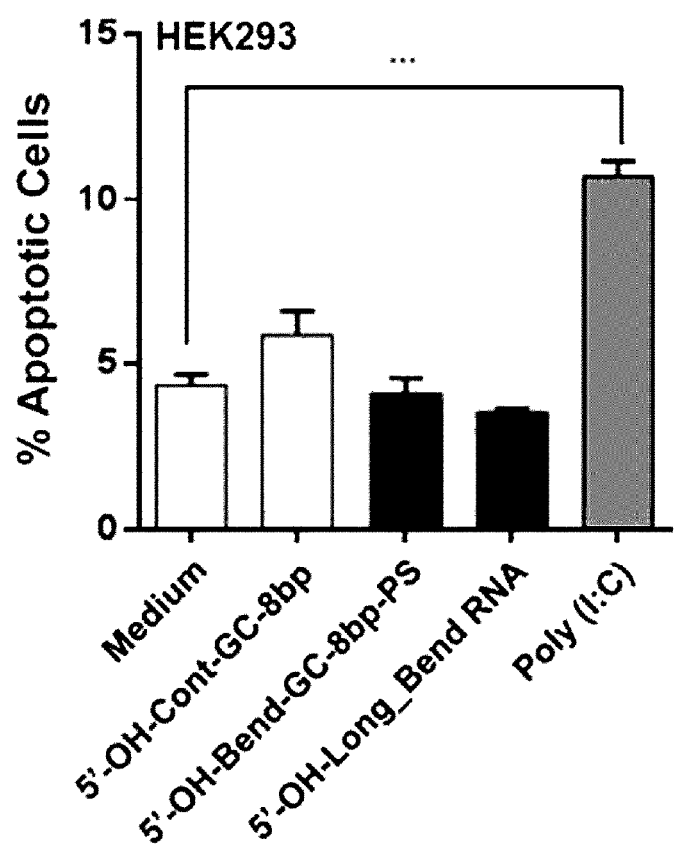
FIG. 6 is a graph showing the apoptosis induction effect of normal cell line (HEK293) using FACS by 5'-OH-Bend-GC-8 bp-PS and 5'-OH-Long_Bend, RNA oligonucleotides prepared according to an example of the present disclosure.

The rate of apoptotic cells is shown in the graph of FIG. 6.

As shown in FIG. 6, 5'-OH-Bend-GC-8 bp-PS RNA oligonucleotide and 5'-OH-Long_Bend RNA oligonucleotide having a bend structure with a hydroxy group at the 5'-end did not induce apoptosis of HEK293 cell line to a significant level, while poly (I:C) induced apoptosis of HEK293 cell line.

In summary, the results of Experimental Examples 3 and 4 showed that 5'-OH-Bend-GC-8 bp-PS RNA oligonucleotide and 5'-OH-Long_Bend RNA oligonucleotide selectively induced apoptosis of cancer cells between normal cells (HEK293) and cancer cells (pancreatic cancer cell; Panc02).

Experimental Example 5: Verification for Apoptosis Inducement Effect of Liver Cancer Cells by 5'-OH-Bend-GC-8 bp-PS Oligonucleotide In accordance with the procedure of Experimental Example 3.1, liver cancer cell line (SNU886; Korean Cell Line Bank, Republic of Korea) was aliquoted in DMEM (WELGENE, USA) and 5'-OH-Bend-GC-8 bp-PS oligonucleotide was treated thereto. Then, the apoptosis effect was investigated using FACS as Experimental Example 3.2.

Figure 7:
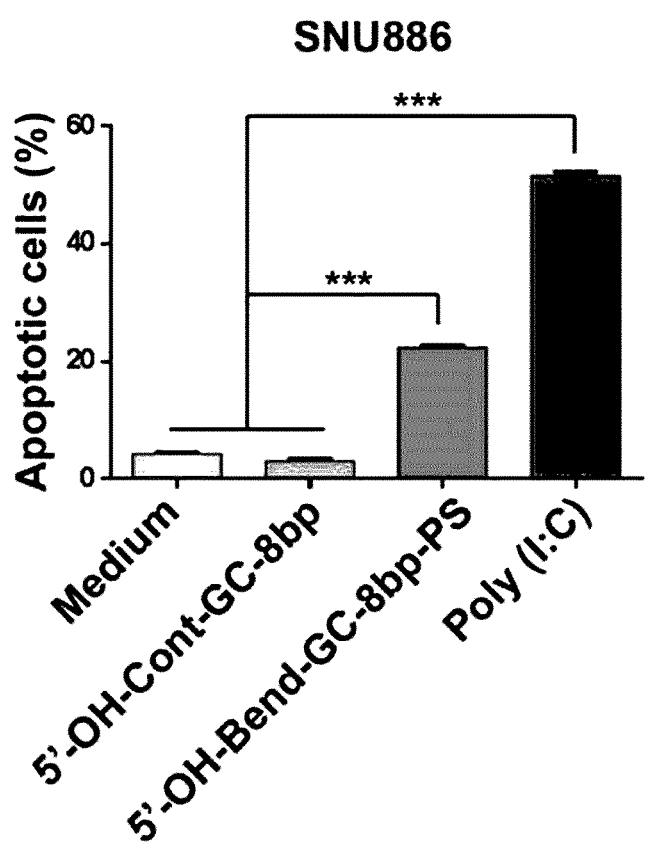
FIG. 7 is a graph showing the apoptosis induction effect of liver cancer cell line (SNU886) using FACS by 5'-OH-Bend-GC-8 bp-PS, an RNA oligonucleotide prepared according to an example of the present disclosure.

The rate of apoptotic cells is shown in the graph of FIG. 7.

As shown in FIG. 7, it was found that 5'-OH-Bend-GC-8 bp-PS RNA oligonucleotide having a bend structure with a hydroxy group at the 5'-end induced apoptosis of liver cancer cell line to a significant level.

Experimental Example 6: Verification for Apoptosis Inducement Effect of Stomach Cancer Cells by 5'-OH-Bend-GC-8 bp-PS Oligonucleotide In accordance with the procedure of Experimental Example 3.1, stomach cancer cell lines (SNU216 and MKN74; Korean Cell Line Bank, Republic of Korea) were aliquoted in DMEM (WELGENE, USA) and 5'-OH-Bend-GC-8 bp-PS oligonucleotide was treated thereto. Then, the apoptosis effect was found using FACS as Experimental Example 3.2.

Figure 8A:
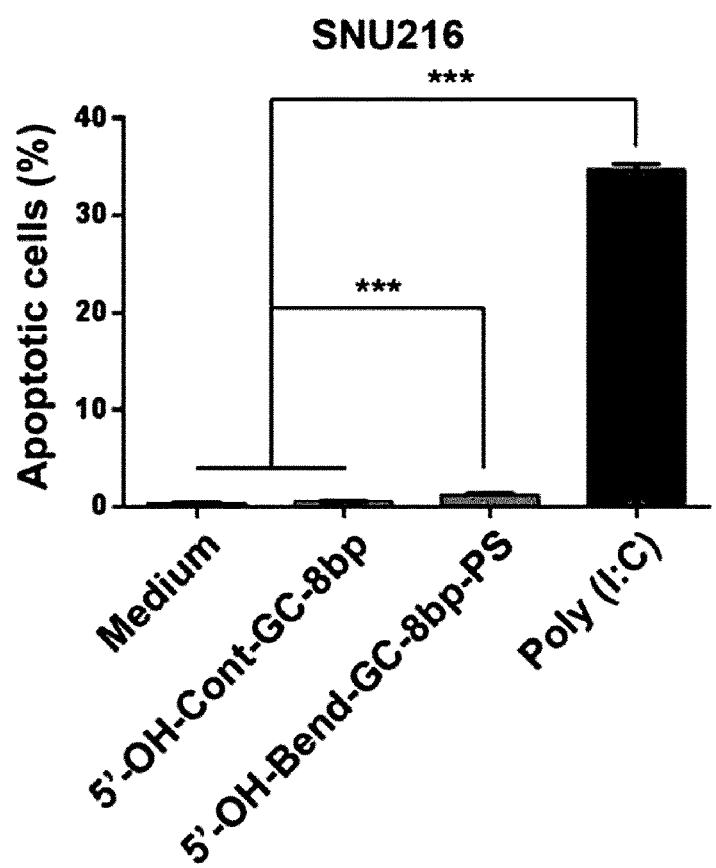
FIGS. 8A and 8B are each graph showing the apoptosis inducement effect of stomach cancer cell lines (SNU216 and MKN74) using FACS by 5'-OH-Bend-GC-8 bp-PS, an RNA oligonucleotide prepared according to an example of the present disclosure.
Figure 8B:
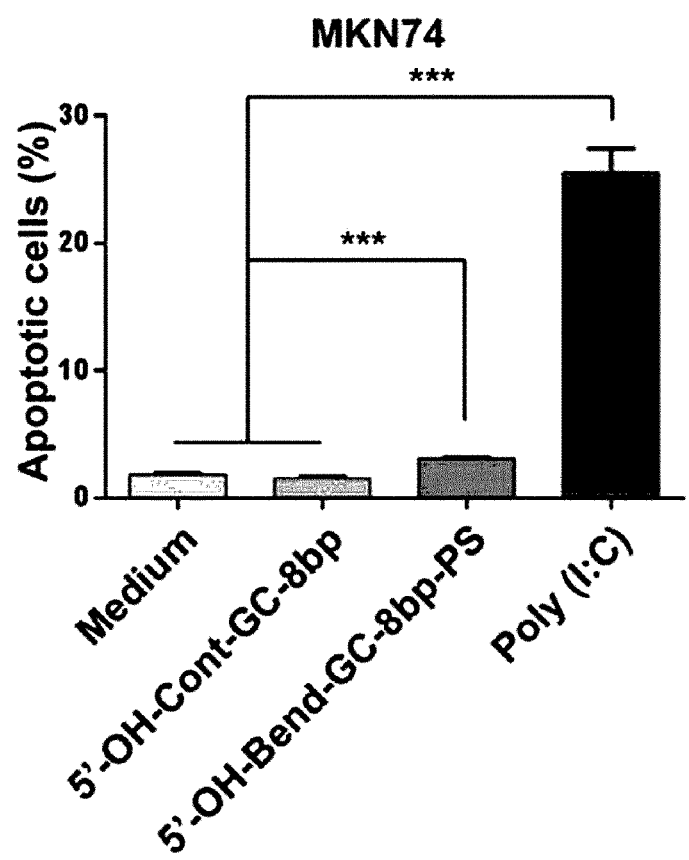

The rate of apoptotic cells is shown in the graph of FIGS. 8A and 8B, respectively.

As shown in FIGS. 8A and 8B, it was found that 5'-OH-Bend-GC-8 bp-PS RNA oligonucleotide having a bend structure with a hydroxy group at the 5'-end induced apoptosis of stomach cancer cell lines to a significant level.

What is claimed is:

1. A method for treating cancer comprising:
   administering to a subject in need thereof an effective amount of a pharmaceutical composition comprising an RNA oligonucleotide,
   wherein the RNA oligonucleotide comprises the base sequence represented by SEQ ID NO:1 (5'-$N_1$GUAGA$N_2N_3$-3') and the base sequence represented by SEQ ID NO:2 (5'-$N_4N_5$UUUGC$N_6$-3'),
   wherein the base sequences are bound to each other by a complementary binding to form double strands having a helical bend structure,
   wherein the 3'-end of the base sequence represented by SEQ ID NO:1 and the 5'-end of the base sequence represented by SEQ ID NO:2 are connected into a loop to form a hairpin structure, and
   wherein the base sequence represented by SEQ ID NO:1 has a hydroxy (OH) group at the 5'-end thereof.

2. The method of claim 1, wherein $N_1$ to $N_6$ are G or C in the base sequence represented by SEQ ID NO:1 or SEQ ID NO:2.

3. The method of claim 2, wherein $N_1$ is G, $N_2$ is C, and $N_3$ is G in the base sequence represented by SEQ ID NO:1 (corresponding to SEQ ID NO:3); and $N_4$ is C, $N_5$ is G, and $N_6$ is C in the base sequence represented by SEQ ID NO:2 (corresponding to SEQ ID NO:4).

4. The method of claim 1, wherein the loop is composed of at least 4 bases.

5. The method of claim 4, wherein the loop is composed of UUCG bases.

6. The method of claim 1, wherein the loop is composed of 4 to 80 bases.

7. The method of claim 6, wherein the loop has a stem structure formed by Watson-Crick base pairing, and the stem structure comprises AU motif composed of AU base pairs.

8. The method of claim 7, wherein the AU motif is composed of 10 to 50 AU base pairs.

9. The method of claim 1, wherein the RNA oligonucleotide has a base sequence represented by SEQ ID NO:7 or SEQ ID NO:8.

10. The method of claim 1, wherein at least one of the phosphodiester bonds in the RNA oligonucleotide is changed to at least one selected from the group consisting of a phosphorothioate bond, a boranophosphate bond and a methylphosphonate bond.

11. The method of claim 2, wherein at least one of the phosphodiester bonds in the RNA oligonucleotide is changed to at least one selected from the group consisting of a phosphorothioate bond, a boranophosphate bond and a methylphosphonate bond.

12. The method of claim 3, wherein at least one of the phosphodiester bonds in the RNA oligonucleotide is changed to at least one selected from the group consisting of a phosphorothioate bond, a boranophosphate bond and a methylphosphonate bond.

13. The method of claim 4, wherein at least one of the phosphodiester bonds in the RNA oligonucleotide is changed to at least one selected from the group consisting of a phosphorothioate bond, a boranophosphate bond and a methylphosphonate bond.

14. The method of claim 5, wherein at least one of the phosphodiester bonds in the RNA oligonucleotide is changed to at least one selected from the group consisting of a phosphorothioate bond, a boranophosphate bond and a methylphosphonate bond.

15. The method of claim 6, wherein at least one of the phosphodiester bonds in the RNA oligonucleotide is changed to at least one selected from the group consisting of a phosphorothioate bond, a boranophosphate bond and a methylphosphonate bond.

16. The method of claim 7, wherein at least one of the phosphodiester bonds in the RNA oligonucleotide is changed to at least one selected from the group consisting of a phosphorothioate bond, a boranophosphate bond and a methylphosphonate bond.

17. The method of claim 8, wherein at least one of the phosphodiester bonds in the RNA oligonucleotide is changed to at least one selected from the group consisting of a phosphorothioate bond, a boranophosphate bond and a methylphosphonate bond.

18. The method of claim 9, wherein at least one of the phosphodiester bonds in the RNA oligonucleotide is changed to at least one selected from the group consisting of a phosphorothioate bond, a boranophosphate bond and a methylphosphonate bond.

19. The method of claim 1, wherein the cancer is selected from the group consisting of pancreatic cancer, liver cancer, stomach cancer, lung cancer, colorectal cancer, rectal cancer, thyroid cancer, esophageal cancer, renal caner, bladder cancer, prostate cancer, cervical cancer, breast cancer, hematologic malignancy, skin cancer, epithelial cancer, brain cancer, central nerves cancer, and ovarian cancer.

* * * * *